US007691614B2

(12) United States Patent
Senapathy

(10) Patent No.: US 7,691,614 B2
(45) Date of Patent: *Apr. 6, 2010

(54) METHOD OF GENOME-WIDE NUCLEIC ACID FINGERPRINTING OF FUNCTIONAL REGIONS

(75) Inventor: Periannan Senapathy, Madison, WI (US)

(73) Assignee: Genome Technologies, LLC, Madison, WI (US)

(*) Notice: Subject to any disclaimer, the term of this patent is extended or adjusted under 35 U.S.C. 154(b) by 316 days.

This patent is subject to a terminal disclaimer.

(21) Appl. No.: 11/031,765

(22) Filed: Jan. 7, 2005

(65) Prior Publication Data

US 2005/0123980 A1    Jun. 9, 2005

Related U.S. Application Data

(63) Continuation-in-part of application No. 09/431,451, filed on Nov. 1, 1999, now Pat. No. 6,846,626.

(60) Provisional application No. 60/151,975, filed on Sep. 1, 1999.

(51) Int. Cl.
*C12P 19/34* (2006.01)
*C12Q 1/68* (2006.01)
*C07H 21/04* (2006.01)
*C07H 21/00* (2006.01)

(52) U.S. Cl. .................. 435/91.2; 435/6; 536/23.1; 536/24.33; 536/25.3

(58) Field of Classification Search ....................... None
See application file for complete search history.

(56) References Cited

U.S. PATENT DOCUMENTS

| 5,200,313 | A | * | 4/1993 | Carrico .......................... 435/6 |
| 5,508,169 | A | | 4/1996 | Deugau et al. |
| 5,512,478 | A | * | 4/1996 | Orser et al. ............. 435/252.33 |
| 5,667,976 | A | * | 9/1997 | Van Ness et al. ................ 435/6 |
| 5,807,679 | A | | 9/1998 | Kamb |
| 6,521,428 | B1 | | 2/2003 | Senapathy |
| 6,528,288 | B2 | * | 3/2003 | Senapathy .................. 435/91.2 |
| 6,846,626 | B1 | * | 1/2005 | Senapathy ..................... 435/6 |
| 2002/0119455 | A1 | * | 8/2002 | Chan .............................. 435/6 |

OTHER PUBLICATIONS

Zhang et al., "Reconstruction of DNA sequenceing by hybridization," Bioinformatics, vol. 19, o. 1, 2003, pp. 14-21.*
Bowie, et al., Deciphering the Message in Proteini Sequences: Tolerance to Amino Acid Substitutions, *Science*, 247:1306 (1990)).
Deeb, S.S., et al., A Splice-Junction Mutation Responsible for Familial Apolopoprotein A-II Deficiency, *Am. J. Hum. Genet.*, 46:822 (1990).
Duyk, G.M., et al., Exon trapping: A genetic screen to identify candidate transcribed sequences in cloned mammalian genomic DNA, *Proc. Natl. Acad. Sci. USA*, 87:8995-9 (1990).

Estivill, X. and Williamson, R., A rapid method to identify cosmids, containing rare restriction sites, *Nucleic Acids Res.*, 15:1415-25 (1987).
Fuentes, J.J., et al., *Alu*-splice PCR: a simple method to isolate exon-containing fragments from cloned human genomic DNA, *Hum. Genet.* 101:346.50(1997.
Harris et al., Distribution and consensus of branch point signals in eukaryotic genes: A computerized analysis, *Nucleic Acid Research*, 18:3015-3019 (1990).
Jendraschak, E. and Kaminski, W.E., Isolation of Human Promoter Regions by *Alu* Repeat Consensus-Based Polymerase Chain Reaction, *Genomics*, 50:53-60 (1998).
Lim, J., et al., A novel splice site mutation in the androgen receptor gene results in exon skipping and a non-functional truncated protein, *Mol. Cell. Endocrinol.*, 131:205 (1997).
Lovett, M., et al., Direct selection: A method for the isolation of cDNAs encoded by large genomic regions, *Proc. Natl. Acad. Sci. USA*, 88:9628-32 (1991).
Melmer et al., Identification of genes using oligonucleotides corresponding to splice site consensus sequences, *Human Molecular Genetics*, vol. 1, No. 6, pp. 433-438, Sep. 1992.
Mueller & Wolfenbarger, (1999), AFLP Genotyping and Fingerprinting, *TREE*, 14:389-394.
Myerowitz, T., Splice junction mutation in some Ashkenazi Jews with Tay-Sachs disease: Evidence against a single defect within this ethnic group, *Proc. Natl. Acad. Sci. USA*, 85:3955 (1988).
O Neill, M.J., et. al., Familial Kallmann Syndrome: A Novel Splice Acceptor Mutationi in the KAL Gene, *Hum. Mutat.*, 11:340(1998).
Reissner, K., et al., Type 2 Gaucher Disease with Hydrops Fetalis inian Ashkenazi Jewish Family Resulting from a Novel Recombinant Allele and a Rare Splice Junction Mutation in the Glucocerebrosidase Locus, *Mol. Genet. Metab.*, 63:281 (1998).
Rommerns, et al., Identification of the Cystic Fibrosis Gene: Chromosome Walkinig and Jumping, *Science*, 245:1059-80 (1989).
Sambrook, J., E.F. Fritsch, and T. Maniatis, (1989), "Molecular Cloning: A Laboratory Manual," Cold Spring Harbor Laboratory Press: New York, NY.
Senapathy, P., Origin of eukaryotic introns: A hypothesis, based on codon distribution statistics in genes, and its implications, *Proc. Natl. Acad. Sci.*, 83:2133-2137 (1986).

(Continued)

*Primary Examiner*—Bradley L Sisson
(74) *Attorney, Agent, or Firm*—Joseph T. Leone, Esq.; DeWitt Ross & Stevens S.C.

(57) ABSTRACT

A method of specifically amplifying desired regions of nucleic acid from a sample is provided. The method uses a plurality of first and second PCR primers, each having a region of fixed nucleotide sequence identical or complementary to a consensus sequence of interest and a region of randomized nucleotide sequence located 5' to, 3' to, anywhere within, or flanking the region of fixed nucleotide sequence; and then amplifying the nucleic acid present in the sample via PCR using the plurality of first and second PCR primers; whereby a subset of the first primers binds to the consensus sequence of interest wherever it occurs in the sample, and a subset of the second primers binds to the sample at locations removed from the first primers such that DNA regions flanked by the first primer and the second primer are specifically amplified.

11 Claims, 2 Drawing Sheets

OTHER PUBLICATIONS

Senapathy, P. et al., RNA splice junctions of different classes of eukaryotes: sequence statistics and functional implications in gene expression, Nucleic Acids Research, vol. 15, No. 17, pp. 7155-7176 (1987).

Senapathy, P., Possible evolution of splice-junction signals in eukaryotic genes from stop codons, *Proc. Natl. Acad. Sci.*, 85:1129-1133 (1988).

Senapathy, P. Distribution and repetition of sequence elements in eukaryotic DNA: New insights by computer-aided statistical analyses,, Molecular Genetics (Life Sci. Adv.), 7:53-65 (1988).

Senapathy, P., et al., 1990. Splice junctions, branch point sites, and exons: Sequence statistics, identification, and applications to the Genome Project, in *Methods in Enzymology, Computer Analysis of Protein and Nucleic Acid Sequences*, Doolittle, R.F., ed., 183:252-278.

Sommer and Tautz, :Minimal homology requirements for PCR, *Nucleic Acids Research*, vol. 17, No. 16, p. 6749, (1989).

Tajima, T., et al., Prenatal Diagnosis of Steroid 21-Hydroxylase Deficiency by the Modified Polymerase Chain Reaction to Detect Splice Site Mutation in the CYP21 Gene, *Endoc. J.*, 45:291 (1998).

Welsh & McClelland, Fingerprinting genomes using PCR with arbitrary primers, *Nucleic Acid Research*, 18:7213 (1990).

Welsh, Petersen, & McClelland, Polymorphisms generated by arbitrarily primed PCR in the mouse: application to strain identification and genetic mapping, *Nucleic Acid Research*, 19:303 (1991).

Wilson, R., et al., 2.2 Mb of contiguous nucleotide sequence from chromosome III of C. elegans, Nature, 368:32-38 (1994).

* cited by examiner

SEQUENCE LISTING

```
<160> NUMBER OF SEQ ID NOS: 5

<210> SEQ ID NO 1
<211> LENGTH: 9
<212> TYPE: DNA
<213> ORGANISM: Artificial
<220> FEATURE:
<223> OTHER INFORMATION: Amplification primer sequence
<220> FEATURE:
<221> NAME/KEY: misc_feature
<222> LOCATION: (1)..(1)
<223> OTHER INFORMATION: "n" at position 1 is C or A.
<220> FEATURE:
<221> NAME/KEY: misc_feature
<222> LOCATION: (6)..(6)
<223> OTHER INFORMATION: "n" at position 6 is C or A.

<400> SEQUENCE: 1 naggtnagt                                                                9

<210> SEQ ID NO 2
<211> LENGTH: 9
<212> TYPE: DNA
<213> ORGANISM: Artificial
<220> FEATURE:
<223> OTHER INFORMATION: Amplification primer sequence
<220> FEATURE:
<221> NAME/KEY: misc_feature
<222> LOCATION: (4)..(4)
<223> OTHER INFORMATION: "n" at position 4 is T or C.
<220> FEATURE:
<221> NAME/KEY: misc_feature
<222> LOCATION: (9)..(9)
<223> OTHER INFORMATION: "n" at position 9 is G or T.

<400> SEQUENCE: 2 actnacctn                                                                9

<210> SEQ ID NO 3
<211> LENGTH: 15
<212> TYPE: DNA
<213> ORGANISM: Artificial
<220> FEATURE:
<223> OTHER INFORMATION: Amplification primer sequence
<220> FEATURE:
<221> NAME/KEY: misc_feature
<222> LOCATION: (1)..(6)
<223> OTHER INFORMATION: "n" at positions 1 through 6 is A, T, C, or G.
<220> FEATURE:
<221> NAME/KEY: misc_feature
<222> LOCATION: (10)..(10)
<223> OTHER INFORMATION: "n" at position 10 is T or C.
<220> FEATURE:
<221> NAME/KEY: misc_feature
<222> LOCATION: (15)..(15)
<223> OTHER INFORMATION: "n" at position 15 is G or T.
```

-continued

```
<400> SEQUENCE: 3
nnnnnnactn acctn                                                      15

<210> SEQ ID NO 4
<211> LENGTH: 7
<212> TYPE: DNA
<213> ORGANISM: Artificial
<220> FEATURE:
<223> OTHER INFORMATION: Amplification primer sequence
<220> FEATURE:
<221> NAME/KEY: misc_feature
<222> LOCATION: (1)..(1)
<223> OTHER INFORMATION: "n" at position 1 is C or T.
<220> FEATURE:
<221> NAME/KEY: misc_feature
<222> LOCATION: (2)..(2)
<223> OTHER INFORMATION: "n" at position 2 is A, G, T, or C.
<220> FEATURE:
<221> NAME/KEY: misc_feature
<222> LOCATION: (3)..(3)
<223> OTHER INFORMATION: "n" at position 3 is C or T.

<400> SEQUENCE: 4 nnnaggt                                                                7

<210> SEQ ID NO 5
<211> LENGTH: 11
<212> TYPE: DNA
<213> ORGANISM: Artificial
<220> FEATURE:
<223> OTHER INFORMATION: Amplification primer sequence
<220> FEATURE:
<221> NAME/KEY: misc_feature
<222> LOCATION: (1)..(4)
<223> OTHER INFORMATION: "n" at positions 1 thorugh 4 is A, G, T, or C.
<220> FEATURE:
<221> NAME/KEY: misc_feature
<222> LOCATION: (5)..(5)
<223> OTHER INFORMATION: "n" at position 5 is C or T.
<220> FEATURE:
<221> NAME/KEY: misc_feature
<222> LOCATION: (6)..(6)
<223> OTHER INFORMATION: "n" at position 6 is A, G, T or C.
<220> FEATURE:
<221> NAME/KEY: misc_feature
<222> LOCATION: (7)..(7)
<223> OTHER INFORMATION: "n" at position 7 is C or T.

<400> SEQUENCE: 5
nnnnnnnagg t                                                          11
```

METHOD OF GENOME-WIDE NUCLEIC ACID FINGERPRINTING OF FUNCTIONAL REGIONS

CROSS-REFERENCE TO RELATED APPLICATIONS

This is a continuation-in-part of application Ser. No. 09/431,451, filed Nov. 1, 1999 (now U.S. Pat. No. 6,846,626, issued Jan. 25, 2005), which claims priority to provisional application Ser. No. 60/151,975, filed Sep. 1, 1999, both of which are incorporated herein by reference.

BACKGROUND OF THE INVENTION

DNA fingerprinting methods have been used for detecting DNA markers in a variety of applications. Examples include detecting DNA markers linked to genetic traits, diagnostic markers for pathogen-borne diseases, forensic genotyping, parentage analysis, and molecular taxonomy. These methods apply to the entire DNA sample, with no specific focus on the functional regions of the DNA. For example, restriction fragment-length polymorphism (RFLP) and amplified fragment-length polymorphism (AFLP) methods rely on the sequences of restriction enzyme recognition sites. See, for example, Mueller & Wolfenbarger (1999) "AFLP Genotyping and Fingerprinting," *TREE*, 14:389-394. These sites occur randomly throughout the human genome, including the intergenic and genic regions, and within the exons and introns of genes, without discrimination. These methods detect variations in DNA found randomly throughout the entire DNA sample, with no focus on the functional regions within a given genome. Similarly, random amplification of polymorphic DNA (RAPD) and DNA amplification fingerprinting (DAF) methods rely on arbitrary sequence primers whose complementary sequences also occur randomly in genomic DNA. See Welsh & McClelland (1990), *Nucleic Acid Research*, 18:7213; and Welsh, Petersen, & McClelland (1991) *Nucleic Acid Research*, 19:303.

It is estimated that approximately 98-99% of human and eukaryotic DNA is non-functional. Variations that occur within the non-functional regions of the genome are not useful for diagnosing or discovering gene defects, or informative variations or mutations. The functional regions of a genome, such as the exons, promoters, and poly A sites, constitute only slightly more than 1% of the human genome. However, current methods of genomic analysis do not specifically target these critically important functional regions of a genome. Thus there remains a long-felt and unmet meet for a method of analyzing, on a genome-wide level, those specific portions of a genome that encode functional DNA sequences.

The human genome harbors the genetic variations for a large number of Mendelian disorders. Many of these disorders have been localized in the genome through linkage studies, and the genes for these disorders are being isolated by different methods. The techniques currently used for isolating genes include: cDNA selection (Lovett, M., et al., *Proc. Natl. Acad. Sci. USA*, 88:9628-32 (1991)), exon trapping (Duyk, G. M., et al., *Proc. Natl. Acad. Sci. USA*, 87:8995-9 (1990)), CpG island identification (Estivill, X. and Williamson, R., *Nucleic Acids Res.*, 15:1415-25 (1987)), hybridization using genomic fragments as probes against cDNA libraries (Rommerns, et al., *Science*, 245:1059-80 (1989)), cloning and sequencing of genomic DNA followed by computer analysis of the possible coding regions (Wilson, R., et al., *Nature*, 368:32-38 (1994)), Alu-splice PCR (Fuentes, J. J., et al., *Hum. Genet.* 101:346-50 (1997)), and Alu-promoter PCR (Jendraschak, E. and Kaminski, W. E., *Genomics*, 50:53-60 (1998)).

These techniques have several limitations. For example, many require analyzing large numbers of subclones to yield meaningful results. Both cDNA selection and hybridization using genomic fragments depend upon gene expression patterns using cDNA or mRNA libraries. Exon trapping requires specialized vectors and cell culture materials; whilst cDNA selection results only in enriching expressed sequences from a specific RNA source and requires much time and effort to determine the origin of the selected cDNAs. Alu-splice PCR also has limitations; it can only identify a few putative exons out of a larger number of true exons, even in a YAC clone. Because none of these methods permit the isolation of all the genes in a given region, usually several of the above methods are used in conjunction to complement one another, thereby achieving more complete results.

Furthermore, these methods are most usually only applied to DNA regions included in vectors such as yeast artificial chromosomes (YACs), bacterial artificial chromosomes (BACs), plasmids, and cosmids. They cannot be applied directly to whole genomic DNA to isolate a majority of the exons of genes contained in the genome. A method for isolating the majority of the flanking regions to a signal sequence, such as the 3' or the 5' splice junction or the promoters, present at numerous locations in a genome with a consensus sequence, would be very advantageous in a variety of genetic studies for discovering and treating major illnesses.

In essence, current methods for specifically amplifying exons present in an unknown genomic DNA are limited in their abilities. The isolation of only exon sequences from a gene will be advantageous for a variety of applications including comparative analysis between individuals. Attempts have been made to use the above methods to accomplish this purpose using genomic DNA fragments cloned into vectors.

For example, the Alu-splice PCR method attempts to isolate exon-containing fragments from cloned genomic DNA. This method utilizes the consensus sequence of splice junctions linked to a restriction enzyme recognition sequence as one primer and the consensus sequence of Alu repeat elements as the other primer to amplify any potential exon sequence that may be present between these primer binding sites in a cloned YAC DNA. However, this method has yielded poor results. For example, in one study, from a total of 128 colonies picked, only ten contained putative exons. Further, out of the few genes present in the two YACs analyzed, none of the nine exons present in one of the genes was isolated. Further still, most of the exons from among the five new genes that possibly existed in these YACs were not isolated except for one or two exons. From among the ten putative exon sequences isolated, six were shorter than 350 nucleotides. As the authors of this study agree, not all genes in a given sample will be identified by Alu-splice PCR, and not all the exons within a given gene will be identified by Alu-splice PCR. There are at least two reasons that explain this outcome: 1) the paucity of conveniently placed Alu repetitive elements; and 2) the limiting factor of specificity of the 5' and 3' splice-site primers; in the best of cases, primer specificity is only eight nucleotides. These inadequate results, even with a relatively short template DNA (YAC) compared to genomic DNA, indicate that this method is not applicable to isolate, in multiplex fashion, the exons of many genes from whole genomic DNA.

SUMMARY OF THE INVENTION

The method disclosed herein specifically targets and amplifies the functional regions of a DNA sample to provide more useful information regarding gene defects, variations, and mutations. The present invention has many practical applications in medicine, biology and agriculture, to name just a few of the fields of interest. It can be used with eukaryotic DNA, as well as prokaryotic DNA. It can be used to analyze mammalian genomes, including the human genome. Because the current method focuses on the functional regions of a genome, and because the results of the method yield an amplification fragment-length fingerprint, the present method has been given the name Functional Genomic Fingerprinting (FGF).

In a preferred version, the method of the present invention uses two sets of PCR primers. Both PCR primers preferably have an overall length of from about 10 to about 36 nucleotides. Both PCR primers also preferably each have a region of fixed nucleotide sequence as well as a region of randomized nucleotide sequence. The fixed nucleotide sequence is dimensioned and configured to hybridize under stringent conditions to a consensus sequence of interest. The randomized nucleotide sequence is preferably located 5' to, 3' to, or flanking the region of fixed nucleotide sequence and a second region of the fixed nucleotide sequence located at a 5'-terminus or a 3' terminus of the first primer.

The consensus sequences may be selected from the group consisting of a promoter sequence, a 3' splice sequence, a 5' splice sequence, an Alu repeat, a tandem repeat, a poly-A site, a lariat signal, a microsatellite sequence, and a homeobox sequence.

By using both sets of primers, the method provided herein amplifies the nucleic acid present in the sample. A subset of the first primers binds to the first consensus sequence, and a subset of the second primers binds to the second consensus sequence, such that DNA regions flanked by the first primer and the second primer are specifically amplified. Once the DNA regions are amplified, the fragments are preferably incorporated into a library.

The method of the present invention may also be used to amplify exons based on Partially-Fixed/Partially-Random primers ("FR Primers"—primer collections where each primer of the collection has an identical fixed portion, and a randomized portion that differs from primer to primer within the collection), where the fixed sequences are splice junction consensus sequences. Splice junction consensus sequences having non-consensus bases may also be used, as well as splice junction FR primers with changed bases. Further, additional bases may be added to the fixed portion of the splice junction FR primers. The number of fixed bases and randomized bases in the splice junction FR primers may also be adjusted to control the number of exons amplified from a DNA sample. In addition, the FR primers having varying fixed bases may also be adjusted.

The method of the present invention also amplifies promoters based on FR primers. The FR primers preferably have promoter consensus sequences as the fixed sequences and a second primer with arbitrary fixed sequences. Non-consensus bases within the promoter consensus sequences may be used as the fixed sequences. Further, the promoter FR primers may be used with changed bases. Additional fixed bases may be added to the fixed portion of the FR primers. Further, the number of fixed and randomized bases in the promoter FR primers may be adjusted to control the number of promoters amplified from a sample DNA.

The method of the present invention may also be used to amplify a polyA site based on FR primers. The FR primers preferably have polyA site consensus sequences as the fixed sequences and a second primer having arbitrary fixed sequences. Alternatively, FR primers with non-consensus bases within the polyA site consensus sequences may be used as the fixed sequences. However, polyA site FR primers with changed bases may also be used. Further, the present method may also be used to adjust the number of fixed bases and randomized bases in the polyA site FR primers to control the number of polyA site amplified from a sample DNA.

The method of the present invention may also be used to amplify lariat site based on FR primers. The FR primers preferably have lariat site consensus sequences as the fixed sequences and a second primer with arbitrary fixed sequences. However, FR primers with non-consensus bases within the lariat site consensus sequences may be used as the fixed sequences, and the bases of the lariat site FR primers may be changed. Further, additional fixed bases may be added to the fixed portion of the FR primers and the lariat FR primers with such added fixed bases. In addition, the present method may be used to adjust the number of fixed bases and randomized bases in the lariat site FR primers to control the number of lariat site amplified from a sample DNA.

The method of the present invention may also be used to amplify the region between promoters and the end of the first exon based on promoter FR primers and the 5' splice junction FR primers. Non-consensus bases may also be used within the promoter FR primers and the 5' splice junction FR primers, as well as the combination of such changed promoter FR primers and 5' splice junction FR primers. Further, additional fixed bases may be added to the fixed portion of the FR primers as well as the promoter and splice junction FR primers with such additional fixed bases. The present method also allows for adjusting the number of fixed bases and randomized bases in the promoter FR primers to control the number of regions between the promoters and the end of the first exons amplified from a sample DNA.

The method of the present invention may also be used to amplify the region between the start of the last exon and the polyA site based on the 3' splice junction FR primers and the polyA site FR primers, using, in addition, the combination of the 3' splice junction FR primers and the polyA site FR primers. Non-consensus bases may also be used within the 3' splice junction FR primers and the polyA site FR primers. Further, the combination of such changed 3' splice junction FR primers and the polyA site FR primers is useful in the present method. Further still, additional fixed bases may be added to the fixed portion of the FR primers, as well as to the 3' splice junction FR primers and the polyA site FR primers with such additional fixed bases. The randomized bases in the 3' splice junction FR primers and the polyA site FR primers may also be adjusted to control the number of regions between the start of the last exon and the polyA site amplified from a sample DNA.

The method of the present invention may also be used to amplify the region between the lariat site and the 3' splice junction using lariat FR primers and the 3' splice site FR primers; the combination of the lariat FR primers and the 3' splice junction FR primers; non-consensus bases within the lariat FR primers and the 3' splice site FR primers; and the combination of such changed lariat FR primers and the 3' splice site FR primers. Additional fixed bases may be added to the fixed portion of the lariat FR primers and the 3' splice site FR primers, as well as to the lariat FR primers and the 3' splice site FR primers having such added fixed bases. The number of regions between the lariat site and the 3' splice site amplified from a sample DNA may be controlled by adjusting the number of fixed and randomized bases used in the lariat and 3' splice site FR primers.

The method of the present invention may finally be used to amplify a region between a given consensus sequence repeated within a sample DNA, such as splice junction or ALU sequence with appropriate FR primers. Further, the FR primers may be based on any sequence within a given genome, and the amplified products may be based on the FR primers.

The method of the present invention may be applied to: identify the genomes of animals, plants and microbes; to identify the genomes of pathogenic bacteria to study and identify disease causing strains; to determine the germ plasma fingerprint of specific and individual plants; to determine and analyze proper parentage for humans and animals; and to determine forensic information as needed.

DETAILED DESCRIPTION OF THE INVENTION

Figure 1:
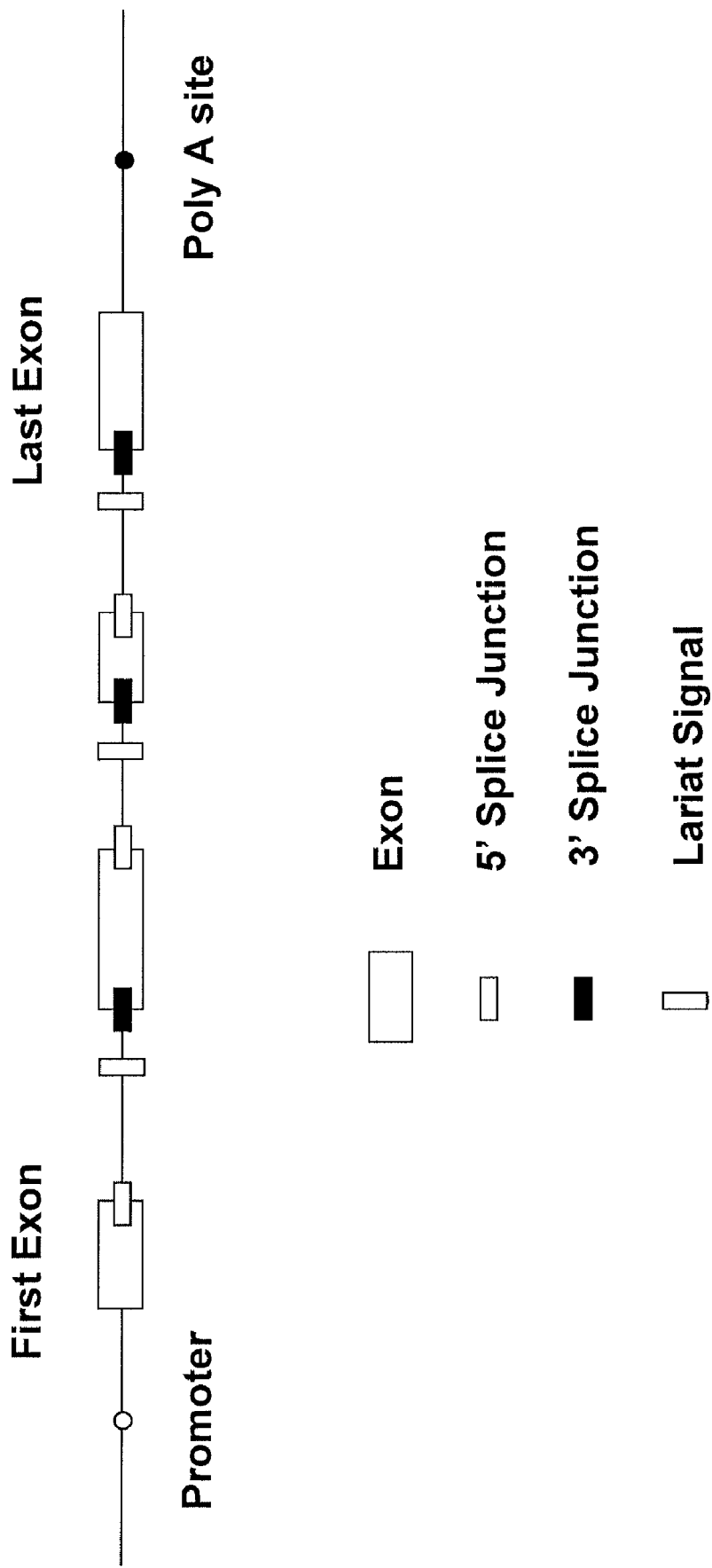
FIG. 1 shows the genetic regulatory sequence regions within a gene.

Abbreviations and Definitions:

The following abbreviations and definitions are used throughout the specification and claims. Terms not expressly defined herein are to be given their accepted definition within the field of genetic and genomic analysis.

5' Splice and 3' Splice Junctions (or Regions)—The regions of DNA defining the upstream and downstream boundaries of an intron. The sequences of 5' splice regions are generally conserved, as are the sequences of 3' splice regions.

Alu Repeats—A family of conserved, short interspersed elements of genomic DNA which contain the recognition sequence for the AluI restriction enzyme (AGCT). In mammals, Alu repeats occur about 1 million times throughout the genome.

Consensus Sequence—Sub-sets or families of relatively short, repetitive DNA sequences which appear throughout eukaryotic (and prokaryotic) organisms. Non-limiting examples of consensus sequences include promoters, Alu repeats, splice regions, etc. Variations may occur within the repetitive sequences. A consensus of the most frequent nucleotides appearing at each position of the repeat is derived, which is then defined as the consensus sequence for the particular type of repeat. For purposes of the present invention, a consensus sequence is any sequence of DNA which is repeated many times throughout a genome and which can be used as a PCR priming site.

Exons—The part of the DNA of a gene that encodes the information for the actual amino acid sequence of the encoded protein.

FR Primers—Partially-Fixed/Partially Randomized Primers: a primer collection wherein each primer of the collection has an identical fixed portion, and each primer has a randomized portion that differs from primer to primer within the collection. The randomized portion can be 5' to the fixed portion, 3' to the fixed portion, or flanking the fixed portion.

Homeobox—A highly conserved sequence of DNA that occurs in the coding region of development-controlling regulatory genes and codes for a protein domain that is similar in structure to certain DNA-binding proteins and is thought to be involved in the control of gene expression during morphogenesis and development.

Introns—A region of DNA in a eukaryotic gene, usually on the order of hundreds to tens of thousands of base pairs long, that is not expressed in the encoded protein molecule or mature RNA. Introns divide the DNA of a single eukaryotic gene into a number of non-contiguous stretches.

Operationally-Linked—When referring to joined DNA sequences, "operationally-linked" denotes that the sequences are in the same reading frame and upstream regulatory sequences will perform as such in relation to downstream structural sequences. DNA sequences which are operationally-linked are not necessarily physically linked directly to one another but may be separated by intervening nucleotides which do not interfere with the operational relationship of the linked sequences.

Poly A Sites—A sequence of DNA that directs the addition of poly A's to a messenger RNA molecule.

Polymerase Chain Reaction (PCR)—A technique in which cycles of denaturation, annealing with a primer pair, and extension with DNA polymerase are used to generate a large number of copies of a desired polynucleotide sequence. See U.S. Pat. Nos. 4,683,195 and 4,683,202 for a description of the reaction. The PCR is widely used in manipulation of nucleic acids.

Primer—Any oligonucleotide capable of binding specifically to a nucleic acid template and priming the PCR. Primers are generally from about 6 to 50 nts long, and preferably from about 10 to 36 nts long.

Promoter—The DNA sequence site where RNA polymerase binds to the beginning of an operon. Once bound, the RNA polymerase travels along the DNA in the 5' to 3' direction and assembles the corresponding RNA sequences. While the promoter functions as the start signal for RNA synthesis, the promoter itself is not transcribed.

Randomized Sequence—A fixed sequence, to which all of the 4 nucleotides (Ns) are linked in a parallel manner, and subsequently repeating this step in a sequential manner. Parallel addition of Ns, (i.e., A, G, C, T) are linked in a parallel manner. Ns are added at the end-nucleotide of a fixed sequence. For example, if the end-nucleotide is G, all four nucleotides are linked to the G, producing GA, GG, GC, and GT. A subsequent addition of N to this primer preparation again will link all the four nucleotides to the 3' end of all the four species of primers, resulting in 16 possible sequences, namely, GAA, GAG, GAC, GAT, GGA, GGG, GGC, GGT, GCA, GCG, GCC, GCT, GTA, GTG, GTC, and GTT. Subsequent repetition of this step will link all the four nucleotides (i.e., Ns) to all the possible sequences that resulted in the previous step (i.e., to the nth randomized nucleotide(s)). This process will generate an exponentially expanding array of random sequences as the number of added Ns increases. All of the possible sequences of length N (4N different sequences) will be linked to the fixed sequence, and will be present in the fully randomized oligonucleotide prepared in this manner.

Signal Sequence—A stretch of DNA or RNA sequence within a gene or a genome that functions as a signal for a molecular activity. For instance, a promoter sequence signals the attachment of an RNA polymerase enzyme to it and the further transcription of the gene. A splice junction sequence signals to the spliceosomal machinery the splicing together of the exons and editing out of the introns in the primary RNA sequence. Poly-A addition site, Alu sequence, homeobox sequence, and microsatellite sequence are other examples of signal sequences.

Template Nucleic Acid or Nucleic Acid Sample—DNA or RNA to be analyzed using the subject method. The source for the nucleic acid to be analyzed is irrelevant. Isolating DNA and RNA from virtually any source is extremely well known. The invention functions with equal success using nucleic acid from any source, including eukaryotic, procaryotic, animal, plant (both monocot and dicot), fungi, algae, and virus nucleic acids, DNA and RNA included, without limitation.

Genetic Engineering:

Many of the steps noted below for the manipulation of DNA, including digesting with restriction endonucleases, amplifying by PCR, hybridizing, ligating, separating and isolating by gel electrophoresis, transforming cells with heterologous DNA, selecting successful transformants, and the like, are well known and widely practiced by those skilled in the art and are not extensively elaborated upon herein. Unless otherwise noted, the DNA protocols utilized herein are described extensively in Sambrook and Russell (2000), "Molecular Cloning: A Laboratory Manual," 3$^{rd}$ Edition, Cold Spring Harbor Laboratory Press: New York, N.Y., ISBN: 0879695765.

General Approach:

The invention is a method for isolating the flanking regions to any type of consensus sequence, or to whole exons from multiple sites in a nucleic acid template or sample, preferably a DNA sample, including a genomic DNA sample, a sub-genomic DNA sample, cloned genomic DNA, individual chromosomes, and a sub-chromosomal DNA sample. The invention is described for use with genomic DNA for illustrative purposes only, not to limit the invention. The invention, for example, enables the specific isolation of most if not all splice junctions (both 5' and 3') or the exon sequences with their flanking regions, from genomic DNA.

Figure 2:
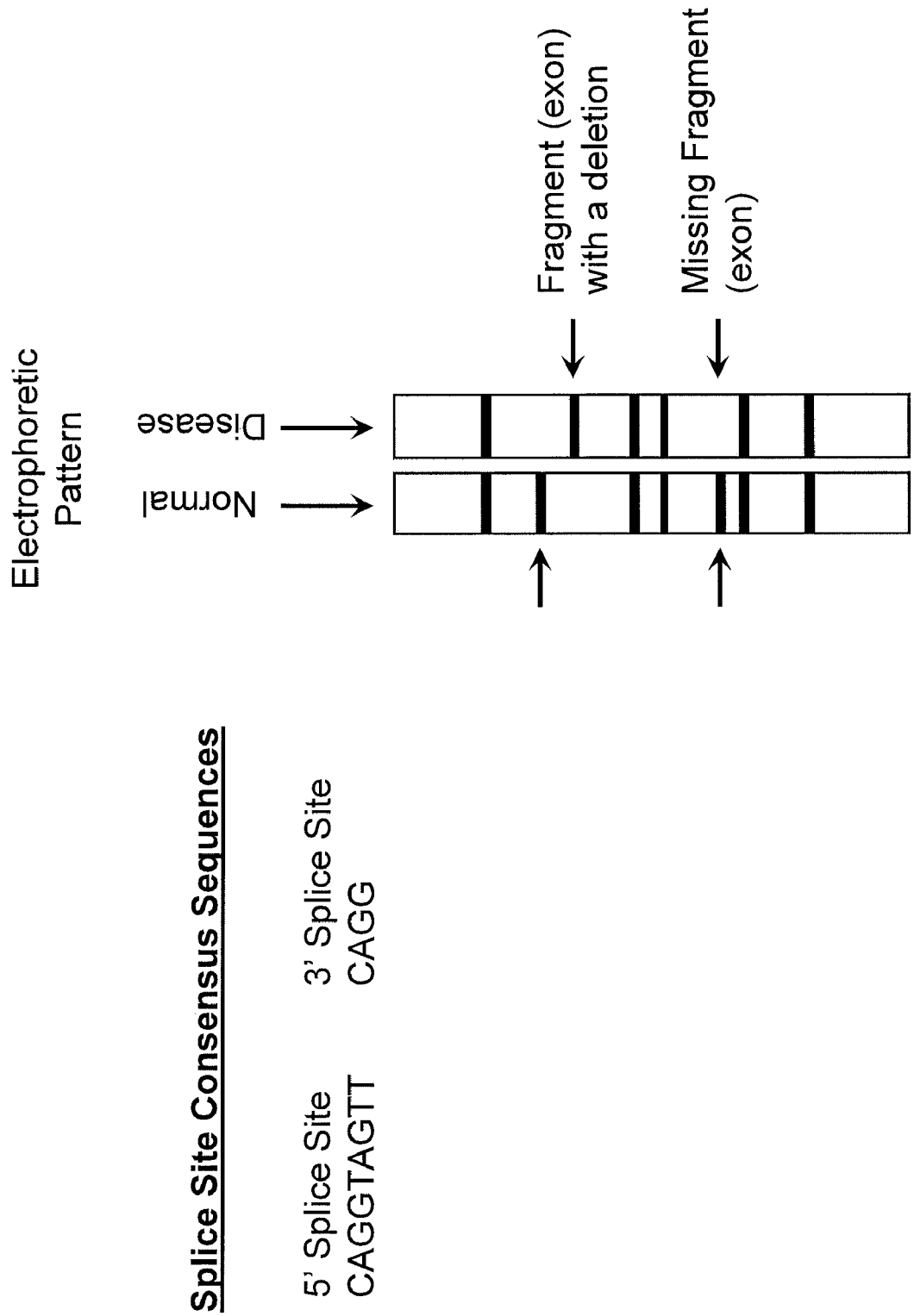
FIG. 2 shows the splice site consensus sequences and the electrophoretic pattern for normal and diseased DNA, with the exon position noted.

In one embodiment, the invention uses the consensus sequence of the 3' splice junction or the 5' splice junction or both for designing a first and/or a second primer which includes, along with the consensus sequence of interest, a stretch of randomized nucleotide sequences (see FIG. 2). The first primer may include a few randomized nucleotides in addition to the consensus sequence such that each of the targeted regions in the genes in a genome will have a specifically matching primer sequence in the primer preparation. A sub-set of the first primers will therefore not only bind to the consensus sequence but also to a few more nucleotides that flank the targeted sequence (on either one side or both sides, depending upon where the random nucleotides N are situated in the first primer relative to the consensus sequence portion of the primer).

Partially-Fixed/Partially-Random (FR) Splice Junction Primers for Functional Genomic Fingerprinting:

The present invention focuses on the functional regions of a genome and is based upon the sequences of regulatory control elements that either flank genes or which are found within genes. Thus, in eukaryotes, the present method targets the consensus sequences surrounding the exons and introns in a given genomic DNA sample. These sequences, known as the splice junction sequences, are then reflected in a "fingerprint" of the genome. Based on the fingerprints of different genomes, the variations within the set of exons between two or more given human (or non-human) individuals, for example, are exposed. Note that the method does not yield a fingerprint of the entire genome, including both functional and non-functional regions. Rather, the method yields a genome-wide fingerprint of only the functional elements of a genome, and more specifically a genome-wide map of splice junctions, exons, and the areas flanking splice junctions. Because mutations causing disease are often found within the splice junctions, fingerprints of the splice junctions are useful in detecting the disease-causing mutations by comparing the fingerprint of a diseased genome with that of a normal genome. Similarly, genetic variations for favorable traits can also be discovered.

This present invention uses the splice junction sequences of a given DNA to amplify specifically the exon sequences present within a target DNA. Because the consensus sequence of the splice junction on the 5' end of an exon is different from that on the 3' end of an exon, two distinct pluralities of Partially-Fixed/Partially-Random primers ("FR Primers") of exons are used in the invention. Each individual FR Primer comprises a fixed portion of sequence that is substantially complementary to the splice junction of interest, and a randomized portion of sequence that is either upstream of, downstream of, or flanks the fixed portion. Within any given plurality of FR Primers, the fixed portion is identical in each individual FR Primer within the plurality. The randomized portion varies between each individual FR Primer within a given plurality of primers. Thus, in an identified plurality of FR Primers, the fixed portion of each individual primer will be identical and the random portion will vary.

The fixed portion of each FR Primer is dimensioned and configured to hybridize specifically to the consensus sequence of one of the two splice junctions (e.g., the 5' splice junction or the 3' splice junction). This enables the FR Primer to bind to a given splice junction specifically, substantially wherever it occurs in the DNA sample. The randomized portion of the FR Primer allows for the presence of individual FR Primers having full-length sequences complementary (or substantially complementary) to the genomic sequences adjacent to or flanking each of the individual splice junction sequences. Thus, a plurality of FR Primers provides a collection of full-length primers capable of specifically binding to, and priming the amplification of, all of the splice junctions and exons (or introns) throughout an entire DNA sample (including whole genomic DNA samples).

While the sequences surrounding the various splice junctions within a genome are different, a suitably configured collection of FR Primers includes at least one individual primer that is dimensioned and configured to hybridize to and to prime amplification of each of the different splice junctions within a given genome. Thus, a plurality of FR Primers containing fully complementary primers for the splice junctions can be fabricated without any prior knowledge of the sequences flanking each splice junction and without any knowledge of the location of the splice junctions within the target DNA. By using appropriately designed FR Primers for the 5' splice junctions and the 3' splice junctions, all (or substantially all) of the exons within a genome can be amplified in one reaction.

In the preferred embodiment of the invention, the fixed portion of the FR Primer is relatively long as compared to the randomized portion. Thus, the probability of an exact complementary match of any given primer within an entire genome is fairly low. Therefore, the non-specific amplification of sequences that are not exons is also quite low. In short, by judiciously designing the primers and running the amplification reaction under stringent conditions, spurious amplification products are minimized or eliminated entirely.

The present invention uses two different pluralities of FR Primers: a first plurality dimensioned and configured to hybridize specifically to the 5' splice junction sequences, and a second plurality dimensioned and configured to hybridize specifically to the 3' splice junction sequences. These two pluralities of FR Primers specifically amplify all (or substantially all) of the exons present within the target DNA. This specificity is largely due to the fact that in mammals, the 5' splice junction consensus sequence is usually about 10 base pairs long. A target sequence of this length is long enough for specific hybridization and amplification, while simultaneously avoiding nonspecific binding at other locations. See Shapiro & Senaphthy (1987), "RNA Splice Junctions of Different Classes of Eukaryotes: Sequence Statistics and Functional Implications in Gene Expression," *Nucleic Acids Research*, 15:7155-7175; Senaphthy, Shapiro, & Harris (1990), "Splice Junctions, Branch Point Sites, and Exons: Sequence Statistics, Identification, and Applications to the Genome Project," *Methods in Enzymology, Computer Analysis of Protein and Nucleic Acid Sequences*, R. F. Doolittle, Ed., 183:252-278; and Senaphthy (1998) "Possible Evolution of Splice-Junction Signals in Eukaryotic Genes from Stop-Codons," *Proc. Natl. Acad. Sci. USA*, 85:1129-1133. The probability of the 5' splice junction sequence occurring randomly within a genome is very low.

Moreover, the 3' splice junction is about 15 base pairs long, and generally comprises about five conserved base pairs and ten partially fixed bases (usually C or T). This is statistically equivalent to 5 fully fixed bases, totaling to 10 fixed bases.

Thus, the juxtaposed pairing of a roughly ten base pair-long 5' splice junction and a five-to-fifteen base pair-long 3' splice junction affords unique (or sufficiently rare) paired priming sites such that the sequences of all exons in a sample of genomic DNA can be amplified specifically and simultaneously. This is true even if we use a 10 base long 5' splice junction sequence with that of the 5 base long 3' splice junction sequence. In short, the statistical likelihood of non-specific occurrences of paired sequences that match the 5' to 3' splice junction pairings is extraordinarily rare. This statistical rarity of non-specific sequences enables, in part, the two pluralities of FR Primers to amplify the splice junction regions and the sequences bounded between them specifically.

In the most preferred embodiment of the invention, at least one individual primer within the first and second pluralities of FR Primers will bind to all of the 5' and 3' splice junction sequences (respectively), because the randomized portions of at least a sub-plurality of the primers will contain a complementary match to the entire splice junction (or a portion of the splice junction and the DNA flanking the splice junction). In other words, the randomized portion of the first and second pluralities of FR Primers contains all of the possible sequences that can occur within the randomized length of the primers. In the preferred embodiment of the invention, the randomized portions of each plurality of FR Primers are fully randomized, with at least one of every possible permutation of random sequence occurring in the plurality. This approach thus provides a full-length, complementary sequence primer at all 5' and 3' splice junctions within the entire DNA sample. While the majority of splice junction sequences conform to the splice junction consensus sequence, by fully randomizing the variable portions of the FR Primers, each plurality of primers incorporates those splice junctions that do not conform to the consensus splice junction sequence. Furthermore, with slight alterations of the splice junction consensus sequences (the fixed portion of the FR primer), a smaller subset of splice junctions that do not conform to the consensus sequences can be bound, and the corresponding exons or surrounding sequences can be amplified.

The method can also be fine-tuned to amplify less than all of the exons in a sample. This is accomplished by adding additional fixed bases to the fixed portion of each FR Primer. From a statistical standpoint, for every additional fixed base that is added to the FR Primers (in addition to the consensus splice junction sequences), the number of amplicons generated from a given DNA sample will be reduced four-fold. For instance, in a plurality of FR Primers wherein each individual primer consists of 16 bases, with ten fixed bases as the splice junction sequence and six fully randomized bases, the change of one randomized base (N) into a fixed base (e.g., G) (across the entire plurality), will reduce the number of exons amplified by that plurality of primers by four-fold. Similarly, if the plurality of 16-base primers are extended by adding an additional four fixed bases to each primer (to yield a 20-base primer having 14 fixed and six random nts), the number of fragments amplified using the plurality of 20-base primers will drop by factor of 256 as compared to the number of fragments amplified using the plurality of 16-base primers.

Any variation within the splice junction sequence of a particular exon potentially prevents that particular exon from successful PCR amplification. Therefore, comparing PCR amplification of DNA samples from two individuals will highlight the absence of this fragment when the set of exon fragments are subjected to gel electrophoresis.

Non-specific amplification of DNA sequences between successively occurring 5' splice junction sequences or between successively occurring 3' splice junction sequences is minimized due to the nature of how these sequences occur in a sample of genomic DNA and due to the limitations of PCR-based amplification. The average distance between successive occurrences of the 5' splice junction sequences in a random DNA sequence is approximately one million bases. The PCR amplification protocol is inherently incapable of amplifying DNA of this length. The successive occurrences of the 3' splice junction sequences is also minimized because the average length between successive occurrences of such sites in a random sequence is also greater than one million bases. Thus, non-specific amplification is naturally suppressed due to the distance between successive appearances of 5'-5' and 3'-3' splice junctions and the limitations of PCR amplification.

There are, however, a few locations in genomic DNA wherein consecutive occurrences of the same site, i.e., the 5' or the 3' splice junction site, occur non-specifically in a forward and reverse complementary directions, such as within intergenic regions or intronic regions. Undesired amplification from these regions can be avoided by careful examination of the fixed portions of the FR Primers and the known sequences of the intergenic/intronic regions of the DNA to be examined. Where undesired amplification is likely to occur, additional fixed bases can be added to the FR Primers to limit the potential number of exons that will be amplified by any given reaction. By running duplicate reactions using different pluralities of FR Primers (pluralities have longer or shorter fixed regions), informative fingerprints can be generated easily.

In a preferred embodiment of the invention, the exon sequences from a given target DNA are first isolated and then cloned into a library. The cloned fragments can then be used to detect variations within the splice junction sequences or the sequences flanking the splice junction sequences.

Cloning the isolated fragments and incorporating them into a library is achieved using an adapter sequence containing a restriction enzyme recognition site on one of the FR Primers, in combination with another restriction enzyme recognition site on the other FR Primers. This combination enables the exon sequences bounded by the 5' splice junction on one end and the 3' splice junction on the other end to be isolated easily using restriction endonucleases that recognize the adapter sequences incorporated into the FR Primers. This approach has the added benefit of avoiding the cloning of non-specific sequences that are bounded by only one of the adapter sequences. (Such a spurious amplicon would not contain the appropriate adapters on both ends, and thus would not be incorporated into the resultant library.)

Eliminating the detection of fragments from non-specific amplification between the successive occurrences of the binding sites for the same primer is accomplished by differentially labeling the two pluralities of FR Primers. For example, the first and second pluralities of FR Primers could be labeled with different radioactive or fluorescent probes. The amplified fragments that contain both labels are those sequences bounded on one end by a primer from the first plurality of FR Primers and on the other end by a primer from the second plurality of FR Primers. This approach excludes those rare-occurring, non-specific sequences from within a target DNA that are bounded by 5'-5' splice junctions or 3'-3' splice junctions. These types of non-specific amplification products would be bounded on both ends by only a single type of label. Thus, they would be eliminated from detection on an electrophoretic gel, chromatogram, or other means of detection.

Amplifying exons bounded by the splice junctions using the two pluralities of FR Primers generates fragments based on the splice junction sequences. (Recall that the fixed region of the primers is designed to hybridize to the splice junctions.) These fragments can be separated on a sequencing gel. (Most exons are shorter than a thousand bases and can be resolved on a sequencing gel. See Senaphthy, P. (1986) "Origin of Eukaryotic Introns: A Hypothesis, Based on Codon Distribution Statistics in Genes," *Proc. Natl. Acad. Sci.* 83:2133-2137.) Because the number and length of these fragments are characteristic of a given DNA sample, the method disclosed herein yields a specific pattern or fingerprint of exons. Each individual tested will yield a unique fingerprint, based upon the occurrence of exons in each individual. Any variation present in the length of the exon sequences in one target DNA as compared to the corresponding fragments in another target DNA is thus revealed as a variation of the exon fragment lengths on the sequencing gel. The fingerprint therefore reveals the insertion or deletion of sequences within an exon fragment from one target DNA with respect to the corresponding fragment in another target DNA.

Herein lies the primary utility of the present invention: exon-length DNA fingerprints (an exon map of a template DNA) are generated, thereby allowing for genome-wide comparisons between individuals from the same species, or from different species. Individual DNA samples can be compared, or pooled DNA samples can be compared. The exon-length fingerprint of an individual can be compared to a "group" fingerprint generated from pooled DNA, etc.

Another type of fingerprint difference can be due to the variations present within the splice junction sequence itself. For instance, consider the 5' splice junction consensus sequence that is used in the plurality of FR Primers as the fixed portion of each primer. Consider also that an exon within a particular gene contains this sequence in the genome of a first individual, but that the corresponding exon within the corresponding gene in the genome of a second individual contains a variation of that 5' splice junction sequence. The DNA fragment corresponding to this exon is present in the exon fingerprint of the first individual, but is absent from the exon fingerprint of the second individual. This is because the fragment in question is not amplified from the DNA of the second individual because the FR Primers would not bind at the particular splice junction due to the variation of the splice junction sequence. The absence of this particular fragment is detected in the comparison of the two fingerprints (e.g., through a pair of sequencing gels run side-by-side). The variation in the splice junction can be as small as one base pair. Conversely, by changing the fixed sequence to non-conforming splice junction consensus sequences, only the variations between such sites between two sample DNAs would be detected.

Thus, there are two types of exon variations that are detected by this procedure. In the first variation, variations in the length of corresponding exons between two different sample DNAs are detected (i.e., exon-length polymorphisms). In this case, an exon of a varying length would be detected in the amplified products from a first sample DNA as compared to the corresponding exon from the amplified products from a second sample DNA. In the second variation, variations in the sequence of the splice junction of one exon in a first sample DNA as compared to that in the corresponding exon in a second sample DNA are detected (i.e., splice junction sequence polymorphisms). In this case, an exon is present in the amplified products of a first sample DNA, but is absent in the corresponding amplified products of a second sample DNA.

The splice junction consensus sequences incorporated into the fixed portion of the FR Primers can be altered to include variations at different positions. Thus, if the same DNA sample is analyzed using different sets of FR Primers, this will cause different subsets of fragments to be amplified from a sample DNA. Thus, using the present approach, there are different sets of DNA fragments of exons that can be generated and compared. Thus, a host of variations can be revealed between two or more samples of DNA.

For example, analysis of a genome using the present invention can reveal crucial variations that may point to disease states or favorable traits (because it is well known that many diseases with genetic causes originate from such variations.) For example, a single nucleotide mutation at the 5' splice junction sequence causes Tay Sachs disease in Ashkenazi Jews. Myerowitz, T. (1988) *Proc. Natl. Aacd. Sci. USA*, 85:3955. A 5' splice junction mutation has been shown to be responsible for familial apolipoprotein A-II deficiency by blocking the splicing of intron 3 from the primary transcript. Deeb et al. (1990) *Am. J. Hum. Genet.*, 46:822. A splice junction mutation in the steroid 21-hydroxylase gene is the most frequently detected mutation in patients with the salt-wasting and simple-virilizing forms of steroid 21-hydroxylase deficiency. Tajima et al. (1998) *Endoc. J.*, 45:291. A type 2 Gaucher disease is the result of a rare splice junction mutation in the glucocerebrosidase gene. Reissner, K. et al. (1998) *Mol. Genet. Metab.* 63:281. A splice acceptor mutation in the KAL gene yields Familiar Kallmann syndrome. O'Neill et. al. (1998) *Hum. Mutat.*, 11:340. A splice site mutation in the androgen receptor gene results in exon skipping and a non-functional truncated protein. Lim et al. (1997) *Mol. Cell. Endocrinol.*, 131:205. Mutations in the promoters and polyA sites also have been to known to cause an increase, decrease, or abolition of gene expression, as well as the synthesis of the particular mutant transcript and therefore the production of particular mutant protein. Therefore, the present method, which isolates specifically a gene's control region(s) from a genomic DNA sample, is a boon to genetic analysis and diagnosis of disease based upon that analysis.

A third type of variation present in the splice junction sequences is also revealed by the present invention. The consensus sequence of a splice junction reflects the statistical majority of occurrences of the specific bases around the splice junctions. There is therefore a minority of splice junctions whose sequence is not present in the consensus sequence. Thus, by altering the bases in the consensus sequences of both 5' and 3' splice junctions in the fixed portion of the first and second pluralities of FR Primers, the subsets of exons that contain the non-consensus splice junction sequences are amplified selectively. These sets of exons can be separately isolated and cloned or analyzed for variations in different genomes.

The important feature of this technology is that it provides a platform method for specifically analyzing defined subsets of exons based on the fixed portions of the splice junction sequences, or other forms of regulatory sequences such as the promoter or polyA sites (see below for a further discussion).

It is known that, in a significant majority of diseases having a genetic basis, the disease is caused by the variation in the splice junction sequences or promoter sequences within particular genes. This present method enables one to fingerprint the genome of an individual with a specific disease and identify any splice junction variations present in the DNA (by comparing the diseased fingerprint to a corresponding DNA fingerprint from another, disease-free, individual). Similarly, it is known that a splice junction created by mutation of a cryptic splice site, can lead to a cryptic exon that has become abnormally functional in a gene. Such a mutation can lead to genetic disease in an individual, for example, in some forms of hypertropic cardiomyopathy. In this instance, the fingerprint of the mutant genome would reveal an extra fragment as compared to the normal genome; additionally the normally present exon would be missing in the diseased individual's fingerprint. There are many instances wherein a mutation in one of the splice junction sequences, say at the 5' splice junction sequence, would lead to the inactivation of that site and the activation of a cryptic 5' splice junction within the downstream intron. This would lead to the extension of the exon sequence into the intron and a longer, aberrant exon sequence. This longer, aberrant sequence could be the cause of a disease. In this instance, the present method would reveal the varying length of this exon as compared to the corresponding exon in the normal DNA sample.

Having the consensus splice junction sequences as the fixed portions sequence of the FR Primers enables the method to detect any variation within the exons or splice junction themselves. However, it does not permit the detection of variations present within the randomized portions of the FR Primers, which bind with sequences surrounding the splice junctions (in the introns or the exons). This is because the presence of the randomized sequences in these regions will bind with any suitably complementary sequence, including those containing mutations.

However, this outcome can be addressed by having the randomized bases interspersed with the fixed bases. As a general proposition, the randomized portion of each FR Primer is either 5' to, 3' to, or flanking the fixed portion of the primer. But, the following procedure enables the recognition of variations within the sequences surrounding the exon splice junction consensus sequence. The randomized portion can be fixed at one or more base positions, in addition to the fixed portion of the consensus splice junction sequence. This allows the FR Primers to bind to only a subset of splice junctions that contain this fixed sequence. At the formerly randomized sites, it enables the detection of mutations or variations relative to the fixed sequence in a particular exon in one DNA sample with respect to the corresponding exon in another DNA sample. The number of bases that are fixed in the randomized portion can be varied to control the range of amplified sequences that include the mutation of interest. The number of reactions required to cover all possible sequences will increase according to the number of fixed bases present in the two pluralities of FR Primers. For example, if three bases in the FR primers' randomized bases were to be fixed and then tested individually, it would require 64 different PCR reactions to cover all of the possible triplet sequences at these three now-fixed locations. However, these PCR reactions could be run in multiplex fashion, using differential labeling to identify the amplicons from any given set of FR Primers. The use of different fluorescent labels in multiplexing is known in the literature. In addition, combinations of variations within the 5' and the 3' splice junctions can also be detected by using multiplexing procedures.

The same principle can be applied to detect variations or mutations on the other side of the FR Primers, for example, on the exon side extending from the fixed portion of the primer. In this instance, this method can be combined with the use of a plurality of FR Primers wherein the fixed portion has an arbitrary sequence or a sequence specifically designed to prime amplification of a known feature. This enables the amplification of fragments surrounding a splice junction sequence, as well as fragments from specific locations within the genome, depending on the sequence of the fixed portion of the second plurality of FR Primers.

Fingerprinting DNA Based on Other Regulatory Sequences, Such as the Promoter, PolyA Sites and Branch-Point Sites:

Regulatory regions such as promoters, polyA sites, and lariat sites comprise short sequences, generally consisting of from about 5 to 8 bases. It is possible to design FR Primers that include them as the fixed portion sequences capable of hybridizing specifically to these types of regulatory sequences. Thus, using a plurality of FR Primers wherein each primer contains a fixed portion capable of hybridizing to a chosen regulatory sequence, and a randomized portion, the regulatory signals can be fingerprinted, analyzed, and compared with other genomes.

The following method is also advantageous when analyzing these regulatory sequences. The promoter in a gene is always followed by the first exon. The initiation of translation of the gene's mRNA starts with the codon ATG, which has been shown to have a short consensus sequence. The 3' end (i.e., the downstream end) of the first exon exhibits the 5' splice junction. Therefore, the promoter sequence, the initiation of translation, and the 5' splice junction of the first exon can be used in various combinations in different pluralities of FR Primers for isolating and analyzing the DNA fingerprints of various samples. Similarly, the last exon ends with a stop codon, which may contain a short consensus sequence. The last exon precedes a polyA site. The last exon also begins with the 3' splice junction. Therefore, the signals of the last exon and the polyA site can be used in various combinations in appropriately designed FR Primer pluralities for isolating and analyzing the fingerprints between various samples.

This method of genome-wide isolation and fingerprinting of exons can be applied to other sequences as well. For instance, the present method can be used to isolate and fingerprint the genome-wide occurrences of sequences bounded by a promoter and the corresponding end of the first exon of every gene. Similarly, the present method can be used to isolate and fingerprint the sequences bounded by the beginning of a last exon and its corresponding polyA site. The method can also be used to isolate and fingerprint fragments bounded by a lariat site and the corresponding start of the exon, a region that generally comprises about 30 bases. N. Harris and P. Senapthy (1990) "Distribution and consensus of branch point signals in eukaryotic genes: A computerized statistical analysis," *Nucleic Acids Research,* 18:3015-3019. The isolated sequences can be cloned into a library. Furthermore, the sequences can be used for fingerprinting the genome-wide sequences surrounding the exons, promoters, and ployA sites by differentially labeling the FR Primers, as noted earlier.

The clone libraries of the regions bounded the promoters and the end of the first exons from a genome are extremely useful. For example, such a library is useful in transfection experiments involving the promoters. Also, the method can be optimized (via appropriate design of the FR Promoters) to isolate from about 10 to about 15 bases upstream of every promoter by using FR Primers having randomized portions upstream or downstream of the fixed portions (the fixed portions being dimensioned and configured to hybridize to the promoters themselves). Similarly, the bases surrounding polyA sites can also be isolated along with the region between the last exon and the polyA site of all of the genes within a given genome.

Isolating the promoter with the first exon simultaneously provides greater specificity to the overall reaction because due to the short promoter sequences there are numerous regions that could nonspecifically conform to the promoter consensus sequence. But by utilizing the longer sequences of the combined promoter/first exon, such non-specific amplification is minimized or eliminated entirely. Similarly, isolating polyA sites in combination with the last exon also confers greater specificity for amplifying only the polyA site (which by itself has a short consensus sequence). If necessary or desired, the promoters alone can be isolated as a library using a second plurality of FR Primers, each individual primer having an arbitrary fixed sequence (i.e., the fixed sequence itself is arbitrary, but the same throughout the entire plurality) to adjust for the average lengths of isolated sequences.

Arbitrary Fixed FR Primer Fingerprinting:

The plurality of FR Primers described herein can also be designed such that the fixed portion of the primers is capable of specifically hybridizing to any consensus sequence of interest within the genome. Because the probability of a given sequence having a length of "n" bases within a given genome follows roughly the probability expected for a random DNA sequence, several approaches can be envisioned by those skilled in the art. For example, a given sequence 10 bases long will occur (statistically) once in a million base pairs within the human genome. Thus, assuming a genome of roughly 3 billion base pairs total, a 10 base-pair motif will occur at about 3000 sites within the entire genome. By using a first plurality of FR Primers having a fixed portion dimensioned and configured to hybridize specifically to the 10-base motif, corresponding to this 10 base long sequence as its fixed portion, the first plurality of FR Primers will prime amplification beginning at the appearance of each 10-base motif. The second plurality of FR primers is then dimensioned and configured to bind to the DNA template at sites that occur within a statistically defined, approximate distance from the binding site of the first plurality of FR Primers. Amplification of a genomic DNA sample using these two pluralities of primers will amplify (specifically) all of the fragments bounded between the two sequences. By comparing the amplification products from two DNA samples amplified using the same pluralities of forward and reverse FR Primers, variations in the length or sequence between any specific fragment is detected. Again, this enables genomic DNA to be fingerprinted and compared, as between, e.g., a diseased individual or population and a non-diseased individual or population.

In the present embodiment, the plurality of the first primers or the plurality of second primers vary in sequence content. The different set of primer pairs will require different set of PCR conditions. Therefore, the PCR reactions will be carried out at three different conditions (low, medium and high) in terms of temperature of melting or buffer conditions that will enable stringent conditions for the different set of primers.

Practical Applications of Fingerprinting Exons:

Exons are known to be of fairly short length, usually under about 600 base pairs. While exons longer than 1000 base pairs exist, they are relatively rare. Thus, if one uses a DNA sequencing gel to distinguish the exon fragments amplified from a sample DNA, according to the present invention, the potential problem of overly-long exons has to be addressed. For example, exons are amplified from BAC DNA, the number of fragments amplified will be small, no more than a few dozen. The probability of two different exons from a BAC DNA clone having exactly the same length is very small. Therefore, the amplification products can be easily separated on a sequencing gel. However, the amplification products from a whole human genomic DNA sample could contain a very large number of exons, possibly several hundred thousand exons. Because most of these fragments are shorter than about 1000 bases, direct electrophoretic separation of the amplicons will generally yield an unresolved smear on the gel. (That or any identifiable band within the resultant gel would likely contain many different exons.)

However, the following method enables DNA fragments to be resolved so that one specific exon sequence per amplified fragment is resolved in the gel, thereby yielding clearly resolved and highly informative "exon fingerprints" or "exon maps." Based on the known size of the human genome and the expected number of genes, approximately 500,000 exons are expected to be found within the human genome. By using pluralities of FR Primers that include the known consensus for the 5' splice junctions and the 3' splice junctions, one would ideally expect that roughly 500,000 exon fragments would be generated. Ideally, however, a set of amplification fragments generated should contain no more than about 1000 different sequences, so that each exon sequence can be cleanly resolved on the sequencing gel.

To move from a potential collection of about 500,000 fragments, to more manageable collections of approximately 1000 fragments per collection, FR Primers are designed that include, on the 5' splice junction side of each primer (and in addition to the fixed consensus sequence) several additional fixed bases. For example, each primer in the plurality would contain the ten fixed bases that hybridize to the consensus sequence, plus an additional five fixed bases located on either the 5' or 3' end of each primer. Fully randomized primers would make up the remaining bases to yield a primer having an overall length from about 20 to 30 bases. From a statistical standpoint, adding five additional fixed bases to each primer within the plurality will reduce the number of suitable hybridization sites for the plurality of primers by slightly more than 1000-fold ($4^5$ fold). A 1000-fold reduction from a starting point of about 500,000 amplicons results in a reaction that yields about 500 amplicons. This is an ideal number to be separated on a sequencing gel. If the number of additional fixed bases is increased to six (from five), the expected number of exon fragments is reduced to about 125, making each fragment length more unique. In each of these examples, only the plurality of FR Primers designed to hybridize to the 5' splice junctions would be altered; the FR Primers designed to hybridize to the 3' splice sites would have a normal consensus sequence as the fixed portion of each primer, with the remaining bases being fully randomized.

Instead of increasing the fixed bases in one plurality of the FR Primers, the number of fixed bases can be increased in both the first and second pluralities of FR Primers. In this fashion, the number of fragments amplified will be in the hundreds, rather than in the thousands. Such a collection of amplification products can be clearly separated on a standard sequencing gel.

The platform technique of the present invention allows the primers to be modified, thereby enabling clear separation of the fragments. This makes it possible to generate a unique fingerprint of a sample DNA.

Advantages and Utility of the FGF Technology:

Because the conventional methods now rely on DNA sequences that occur in a random manner within a sample DNA for fingerprinting, these conventional approaches do not focus on the functional aspects of genes within the DNA. However, the present invention focuses directly on the functional areas of genomic DNA. This ability provides a tremendous capability for identifying variations that directly affect genes, such as those involved in genetic diseases. Many human diseases are caused by the variations or mutations in regulatory sequences such promoters, splice junctions, poly A sites, or the coding sequences contained within exons; all of which together constitute a very small portion of the whole genome. The method presented herein is able to analyze these phenomena more efficiently because the method focuses on the regulatory regions of genes that occur throughout the sample DNA. By taking advantage of the consensus sequences of the regulatory sites, rather than simply random sequences occurring at statistically random spots throughout the genome, the present method enables FR Primers to be designed to include fixed portions that hybridize specifically the consensus sequence of interest. The randomized portion of the FR Primers enables all the possible sequences complementary to the full length of the FR Primers to be amplified, thus providing a full-length primer with a complete complementary sequence at every occurrence of a given regulatory site throughout the sample DNA. Because these sites are directly involved in the amplification of the DNA fragments bounded by such sites, amplification using the FR Primers generates a fingerprint of the functional DNA regions, and thereby reveals any variations of the sequences at these sites, as well as the variation of length of DNA regions bounded by such sites. Thus, mutations within these sites are detected by the presence or absence of a fragment in one fingerprint compared to another.

If a mutation is associated with a particular disease, then the comparison of the DNA fingerprint from an individual with the disease to that from a normal individual will reveal the affected DNA fragment and the affected gene. Thus, the specific fingerprint generated by the subject invention provides the means to diagnosis a genetic-based disease. By comparing the DNA a set of individuals afflicted with a particular disease to the DNA from a set of normal individuals (using the present invention), the specific variation associated with the disease can be identified. Once the affected exon fragment(s) (or other fragments involving promoters or polyA sites) in a disease are identified, the gene containing that exon can be identified by searching for the gene containing that exon sequence in the human genome sequence.

Additionally, there are many genetic variations among the normal individuals that can be identified by this method. However, these variations within the normal population do not correlate with the fingerprint yielded by the DNA from the individuals with the disease. Thus, comparing the two sets of maps reveals the variations that are present only in the individuals with the disease and absent in the normal individuals. Because these genetic mutations or variations are presumably present in newborns and/or the parent(s), the DNA from newborns will also reveal the variation, thus predicting the potency for the disease later in life. Thus, the present method is ideal for the predictive diagnostics of genetic-based diseases.

Direct Disease Gene Discovery Based on FGF:

An interesting aspect of the present invention is that the gene whose defect causes a disease can be identified from the genome sequence directly. The exon fragment can be isolated and sequenced and the gene wherein it is located can be determined from the entire genome sequence. Thus this method not only enables the diagnosis of the disease before the onset of the disease, but also possibly the development of a medical treatment based on the particular gene found to be associated with the disease. This gene and its protein products can be used to develop pharmaceutical drugs or small molecular ligands for protein and gene therapy.

The same method can also be applied to detect desirable traits within human individuals. A group of individuals with the desirable characteristic expressed as a family trait could be compared with another group of individuals whose family does not exhibit this particular trait. The fingerprint of the genomes enables the identification of the genes causative of the particular trait.

Many genetic variations that are nonspecific relative to a disease or trait can be uncovered in the fingerprints. However, these occur randomly in both the normal group and the disease group. Specific variations, found in the regulatory regions, occur only among the disease group, indicating an association between the variation and the disease or trait. Commercially available software programs can be used for assisting the analyses of correlations between a particular fragment sequence and variations in the disease state.

This method disclosed herein can be applied to DNA from any source, be it derived from animal, plant, or microbial sources. It can be used for diagnostic purposes, parentage analysis, and forensic analysis. The fingerprints that ensue from this invention are thus very useful in many applications.

Designing the FR Primers:

In the preferred embodiment, FR Primers are designed with the fixed portions of the primers being designed to hybridize to splice junctions. Thus, the first plurality of FR Primers are designed to hybridize to the direct splice junction sequence, and the second plurality of FR Primers are designed to hybridize to the reverse complement of the splice junction sequence.

The following chemical structure depicts the 5' splice junction sequence (at the end of exon/start of intron).

(SEQ. ID. NO: 1)

The sequence complementary to the 5' splice junction (running 5'→3' on the reverse strand) is depicted below.

(SEQ. ID. NO: 2)

The primer used for amplifying the exon (i.e., for amplifying the sequence from the end of the exon into the exon upstream) comprises the following sequence including the randomized bases ("N"). This is the reverse complement primer that will amplify the exon sequence from the end of the exon upstream. (The Ns can also be located on the 3' end of the primer.)

(SEQ. ID. NO: 3)

The 3' splice junction consensus sequence (at the end of intron/start of exon) is the following, with a stretch of 10 cytosine or thymine bases.

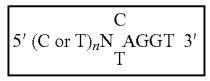
(SEQ. ID. NO: 4)

Because this sequence is present at the start of the exon, this splice junction sequence will be used as the forward (direct) primer, which will amplify the sequence from the start of the exon into the exon downstream. The following primer with Ns could be used, where the number of Ns or ns could be varied. (The Ns can also be located on the 3' end of the primer.)

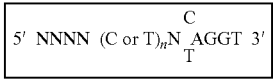
(SEQ. ID. NO: 5)

---

What is claimed is:

1. A method of specifically amplifying desired regions of nucleic acid from a sample containing nucleic acid, the method comprising:

(a) providing a plurality of first polymerase chain reaction (PCR) primers, each first primer having a region of fixed nucleotide sequence dimensioned and configured to hybridize to a first consensus sequence selected from the group consisting of a promoter sequence, a 3' splice sequence, a 5' splice sequence, an Alu repeat, a tandem repeat, a poly-A site, a lariat signal, a microsatellite sequence, and a homeobox sequence;

(b) providing a plurality of second PCR primers, each second PCR primer having a region of fixed nucleotide sequence dimensioned and configured to hybridize to a second consensus sequence corresponding to the first consensus sequence and selected from the group consisting of a promoter sequence, a 3' splice sequence, a 5' splice sequence, an Alu repeat, a tandem repeat, a poly-A site, a lariat signal, a microsatellite sequence, and a homeobox sequence; and then (c) amplifying the nucleic acid present in the sample via the PCR using the plurality of first PCR primers and the plurality of second PCR primers under conditions sufficiently stringent such that a subset of the plurality first primers binds specifically to the first consensus sequence, and a subset of the plurality of second primers binds specifically to the corresponding second consensus sequence, and the nucleic acid flanked by the first primer and the second primer is specifically amplified to yield amplicons.

2. The method of claim 1, wherein the sample containing nucleic acid contains genomic DNA.

3. The method of claim 1, wherein the sample containing nucleic acid contains eukaryotic genomic DNA.

4. The method of claim 1, wherein the sample containing nucleic acid contains human genomic DNA.

5. The method of claim 1, wherein the sample containing nucleic acid contains prokaryotic DNA.

6. The method of claim 1, wherein the sample containing nucleic acid contains RNA.

7. The method of claim 1, wherein step (a) comprises providing a plurality of first primers having an overall length of from about 10 nucleotides to about 36 nucleotides, and step (b) comprises providing a plurality of second primers having an overall length of from about 10 nucleotides to about 36 nucleotides.

8. The method of claim 1, further comprising: (d) incorporating the amplicons of step (c) into a library.

9. The method of claim 1, further comprising: (d) separating the amplicons of step (c) based on their molecular weight.

10. The method of claim 1, further comprising: (d) separating the amplicons of step (c) by gel electrophoresis.

11. The method of claim 1, further comprising (d) separating the amplicons of step (c) by gel electrophoresis to yield size-segregated amplicons; and then (e) incorporating the size-segregated amplicons of step (d) into a library.

* * * * *